United States Patent [19]

Mutsch et al.

[11] 3,981,914

[45] Sept. 21, 1976

[54] N-ALKYLSULFONYLPERFLUOROALK-ANESULFONANILIDES

[75] Inventors: Edward L. Mutsch, Woodbury Township, Washington County; Joseph Kenneth Harrington, Edina, both of Minn.

[73] Assignee: Minnesota Mining and Manufacturing Company, St. Paul, Minn.

[22] Filed: Aug. 3, 1971

[21] Appl. No.: 168,736

[52] U.S. Cl. .......................... 260/556 F; 260/465 E; 260/556 SN; 71/72; 71/76; 71/103
[51] Int. Cl.² ...................................... C07C 143/74
[58] Field of Search ........ 260/556 F, 556 SN, 465 E

[56] References Cited
UNITED STATES PATENTS 3,661,990   5/1972   Harrington ...................... 260/556 F

FOREIGN PATENTS OR APPLICATIONS 1,579,473   7/1969   France ............................ 260/556 F

*Primary Examiner*—Sherman D. Winters
*Attorney, Agent, or Firm*—Alexander, Sell, Steldt & DeLaHunt

[57] ABSTRACT

N-alkylsulfonyl and N-haloalkylsulfonyl-substituted perfluoroalkanesulfonanilides and processes for their preparation are disclosed. These compounds and their compositions are useful as herbicides and plant growth modifiers.

10 Claims, No Drawings

N-ALKYLSULFONYLPERFLUOROALKANESULFONANILIDES

This invention relates to N-alkylsulfonyl and N-haloalkylsulfonyl-substituted perfluoroalkanesulfonanilides and processes for their preparation. These compounds and their compositons are useful as herbicides and plant growth modifiers, particularly as pre-emergence and post-emergence herbicides. Plants may be treated with the compounds of the invention as seeds or at various stages of growth, from seeds onward.

The invention also includes processes for the preparation of the compounds, compositions containing them and methods for their use as herbicides, and plant growth modifiers.

It is an object of the invention to provide compounds which modify the growth of plants, i.e. compounds which prevent, alter, destroy or otherwise affect the growth of plants.

It is a further object of the invention to provide a method for controlling unwanted plants.

Still other objects of the invention will be made apparent by the following specification.

DETAILED DESCRIPTION

According to the present invention, there is provided a class of compounds having the general formula:

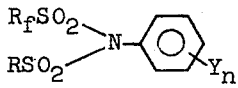 I wherein $R_f$ is perfluoroalkyl of one to two carbon atoms, R is lower alkyl or lower haloalkyl, Y is selected from halogen, nitro, cyano, alkyl, haloalkyl, alkoxy, haloalkoxy, alkylthio, haloalkylthio, alkanoyl, haloalkanoyl, alkanoylamino, haloalkanoylamino, alkylsulfinyl, haloalkylsulfinyl, alkylsulfonyl, haloalkylsulfonyl, alkylsulfonato and haloalkylsulfonato and $n$ is 0-5. When $n$ is 0, the phenyl ring is unsubstituted (except for the amide nitrogen of the formula). Preferably $n$ is 0-2, most preferably $n$ is 0.

It has been found that compounds wherein $R_f$ is trifluoromethyl or perfluoroethyl are very active as herbicides. It appears critical for maximum herbicidal activity that $R_f$ contain one or more fully fluorinated carbons. Compounds wherein $R_f$ contains hydrogen atoms in place of one or more fluorine atoms are much less active or inactive as herbicides. As the number of carbon atoms in $R_f$ increases, cost of the compound increases without a corresponding increase in herbicidal effectiveness. For this reason compounds wherein $R_f$ is trifluoromethyl are preferred.

The lower alkyl and lower haloalkyl R groups normally contain from one to four carbon atoms. The compounds are particularly effective herbicides when R contains one carbon atom, and compounds wherein R is methyl are preferred.

Normally the Y groups contain no more than four carbon atoms each. Presently preferred Y groups are halogen (particularly chlorine, fluorine and bromine), haloalkyl and alkylthio. When more than one substituent is present, the substituents may be the same or different.

The compounds of the invention are generally prepared by the reaction of a perfluoroalkanesulfonanilide in the form of its salt with an alkane-or haloalkanesulfonylating agent of the formula $RSO_2Q$ wherein R is as defined hereinabove and Q is halogen selected from fluorine, chlorine and bromine or the residue of an anhydride, that is the group $RSO_2O-$.

The perfluoroalkanesulfonanilides and alkane- and haloalkanesulfonylating agents are generally known to the art, and/or are prepared according to known synthetic methods. Salts of the perfluoroalkanesulfonanilides which are useful in this process are alkali metal, alkaline earth, aluminum and amine salts. They are readily formed and are known, as a class, to the art.

Suitable sulfonylating agents include methanesulfonyl chloride, chloromethanesulfonyl chloride, trifluoromethanesulfonyl fluoride, trifluoromethanesulfonic anhydride, difluoromethansulfonyl chloride and the like.

The reaction is generally run by converting the perfluoroalkanesulfonanilide to its salt in situ by reaction with a base in non-reactive solvent then adding the sulfonylating agent and allowing the reaction to run until complete. Many bases are suitable, among them inorganic bases such as sodium hydride and metal oxides, hydroxides, carbonates, bicarbonates and alkoxides. Sodium salts are preferred since they are generally available and less expensive. Organic bases which are not reactive with the sulfonylating agent (such as tertiary amines, for example N,N-dimethylaniline, triethylamine and the like) may also be used. In general the reaction temperature will vary, from the freezing point to the boiling point of the solvent used, depending upon the reactivity of the reactants. In some cases the reaction proceeds at a satisfactory rate at room or ice bath temperatures. It is usually preferred to accelerate the rate of reaction, in most cases, by heating the reaction mixture to its reflux temperature and maintaining it at this temperature for about one to twenty hours. Ordinarily, the mixture is then filtered to remove the metal or amine salt which is formed as a by-product, then the solvent is removed in vacuo. The residue may contain unreacted starting material which is removed by suspending the residue in water. The desired product is then isolated by extracting with an organic solvent such as dichloromethane, chloroform or diethyl ether. Alternatively the residue may be dissolved in an organic solvent and the solution washed with water and base. The solution is dried, the solvent is removed in vacuo and the residue is purified further, if necessary, by conventional techniques. Usually recrystallization is satisfactory.

Suitable solvents are those in which the salts of perfluoroalkanesulfonanilides have some solubility, and which are non-reactive, such as acetone, 1,2-dimethoxyethane, diethyl ether, diisopropyl ether, chloroform, dichloromethane and the like.

The herbicidal activity of the compounds of the invention has been determined by standard screening methods against both broad-leafed plants and grasses. They are active against broad-leaves and grasses both pre-emergence and post-emergence.

In order to control unwanted plants, the compounds of the invention can be used alone as herbicides, for example, as dusts or granules of the compounds, or preferably they may be applied in formulations containing the active ingredients in a horticulturally acceptable extending medium. Thus, the herbicidal composition applied to the plants may contain from about 5 to 100 percent of the active compound.

The formulations are comprised of one or more active ingredients and one or more herbicidal adjuvants and/or carriers. Specific formulations are useful to facilitate the application of the compounds and to achieve specific biological objectives such as controlling the availability of the herbicide, improving adherence to plants, and the like, as is well known to those skilled in the art.

The compounds of the invention may be formulated as wettable powders, emulsifiable concentrates, aqueous or non-aqueous solutions and/or suspensions, granules, dusts and the like. Said compounds as such can be finely divided and dispersed or suspended in any of the usual aqueous media, in which they are stable, or if appropriate salts are used, a solution may be made. Spreading agents, wetting agents, sticking agents or other adjuvants can be added as desired.

When emulsifiable concentrates are prepared the active ingredient can be present in concentration of about 5 to 60% or more, depending upon its solubility, but it has been found that the compounds of this invention are preferably used in a concentration of 20 to 30%. The units of concentration are weight per unit weight. The active ingredients are soluble in common organic horticultural solvents such as benzene, toluene, xylene, dichloromethane, chloroform, hexane and heptane or less highly refined aromatic or aliphatic hydrocarbons and mixtures thereof. Examples of these are coal tar fractions, straight run petroleum distillates, thermolytically or catalytically cracked hydrocarbon oil, gas oil, light lubricating oil fractions, kerosene, mineral seal oil, and the like. In appropriate cases, oxygenated solvents such as ketones may be used in or as the carriers. These concentrates can be dispersed in water to permit the use of an aqueous spray. A mixture with a small amount of an organic surface active agent capable of lowering the surface tension of water is preferred, so as to produce more or less stable emulsions.

Examples of surface active agents variously known as dispersing agents, wetting agents or emulsifying agents comprise soft or hard soaps, morpholine or dimethylamine oleate, sulfonated fish, castor and petroleum oils, sodium salts of lignin sulfonic acid, alkylated aromatic sodium sulfonates, such as decylbenzene sodium sulfonate, dodecylbenzene sodium sulfonate, butyl or other amine salts of decyl or dodecylbenzene sulfonic acid, sodium lauryl sulfate, disodium monolauryl phosphate, ethylene oxide condensation products of alkyl phenols, as for example octyl phenol, ethylene oxide condensation products of tall oil and ethylene oxide condensation products of higher alcohols or higher mercaptans. Mixtures of two or more surface active agents are also feasible. Generally, the surface active agent will comprise only a small proportion of the composition, say 0.1-15% by weight of the toxicant.

The formulation of dry compositions for application as granules, dusts or for further dilution with liquid carriers is readily accomplished by mixing the toxicant with a solid carrier. Such solid carriers will be of various sizes from dust to granules. The techniques for such formulations are well known to the art. Suitable carriers include charcoal, talc, clay, pyrophyllite, silicas, fuller's earth, lime, diatomaceous earth, flours such as walnut shell, wheat, soya bean, cottonseed and wood flours, magnesium and calcium carbonate, calcium phosphate and the like. Powders may be granulated by the use of suitable binders such as cellulose derivatives, for example ethyl or carboxymethyl, corn syrup, and the like. The compounds or the above formulations are applied by spraying, spreading, dusting or the like. The rate of application will of course vary, but the more active compounds of the invention exhibit satisfactory control of broadleaf and grass weeds at the application rate of about 1 to 15 pounds per acre. It is of course to be expected that local conditions, for example, temperature, humidity, moisture content of the soil, nature of the soil, and the like, may require greater or smaller amounts. Effective resolution of these factors is within the skill of those versed in the herbicidal art. Likewise it is apparent that not all of the compounds included within the scope of the invention have equal activity.

The herbicidal compositions may contain one or more of the herbicidal compounds set out hereinbefore as the sole active species, or they may contain in addition thereto other biologically active substances. Thus insecticides and fungicides may be incorporated in the compositions. Further, if desired, the herbicidal compositions may contain fertilizers, trace metals or the like and when applied directly to the soil may additionally contain nematicides, soil conditioners, plant growth regulators, and/or herbicides of similar or different properties.

The compounds of this invention are broadly active as herbicides. However, many of the compounds of the invention also show various types of plant growth modifying activity. Plant growth modification as defined herein consists of all deviations from natural development, for example, defoliation, stimulation, stunting, retardation, desiccation, tillering, dwarfing, regulation and the like. This plant growth modifying activity is generally observed as the compounds of the invention begin to interfere with certain processes within the plant. If these processes are essential, the plant will die if treated with a sufficient dose of the compound. However, the type of growth modifying activity observed varies among types of plants. It has been found that with certain compounds of the invention, herbicidal activity can be separated from certain plant growth modifying activities by controlling the rate of application.

The following examples are given for the purpose of further illustrating the procedures of the present invention, but are not intended, in any way, to be limiting on the scope thereof. Thus, one detailed example is given for the purpose of illustrating the general synthetic procedure of the invention and number of examples of compounds of the invention wherein $R_f$, R, $n$ and Y are varied are given in table form. It will be understood, however, that these examples are given for the purpose of illustrating the invention. They are not intended to be limiting on the scope of the invention. The melting points in the examples are uncorrected.

EXAMPLE 1

Sodium carbonate (2.97 g., 28 mmole) and 4-methylthiotrifluoromethanesulfonanilide (6.77 g., 25 mmole) in acetone (100 ml) are stirred vigorously for two hours, then methanesulfonyl chloride (3.21 g., 28 mmole) is added in one portion. Stirring is continued at room temperature and maintained at reflux for about four hours. The reaction mixture is filtered and the filtrate is evaporated in vacuo. Water (100 ml) is added and the mixture is extracted with three 50 ml. portions of chloroform. The organic extracts are dried, then filtered and the solvent is removed by evaporation in vacuo. The residue of N-methylsulfonyl-4-methylthiotrifluoromethanesulfonanilide is recrystallized from ethanol, m.p. 112°–114° C.

| Analysis | %C | %H | %N |
|---|---|---|---|
| Calculated for $C_9H_{10}F_3NO_4S_3$: | 31.0 | 2.9 | 4.0 |
| Found: | 31.5 | 3.0 | 4.0 |

Some examples of compounds of the invention wherein $R_f$ is trifluoromethyl and R is methyl, made using the procedure described specifically in Example 1, are given in Table I.

TABLE I

| Example No. | Compound | Melting Point (in °C) |
|---|---|---|
| 2 | N-methylsulfonyl-2,4-dichlorotrifluoromethanesulfonanilide | 157–159.5 |
| 3 | N-methylsulfonyl-2-methylthiotrifluoromethanesulfonanilide | 113–114 |
| 4 | N-methylsulfonyl-4-fluorotrifluoromethanesulfonanilide | 91–93 |
| 5 | N-methylsulfonyl-4-bromotrifluoromethanesulfonanilide | 107–111 |
| 6 | N-methylsulfonyl-4-fluoro-3-methyltrifluoromethanesulfonanilide | 103–105 |
| 7 | N-methylsulfonyl-2,5-dichlorotrifluoromethanesulfonanilide | 106–112 |
| 8 | N-methylsulfonyl-4-nitrotrifluoromethanesulfonanilide | 164–166 |
| 9 | N-methylsulfonyl-4-chlorotrifluoromethanesulfonanilide | 86–92 |
| 10 | N-methylsulfonyl-5-acetamido-2-chlorotrifluoromethanesulfonanilide | 171–174 |
| 11 | N-methylsulfonyl-5-acetamido-2-methyltrifluoromethanesulfonanilide | 156–165 |

Examples of compounds of the invention wherein $R_f$ and R as well as Y and n are varied are prepared using the general procedure of Example 1 but varying the anilide and/or the sulfonyl halide used and are given in Table II.

TABLE II

| Ex. No. | STARTING MATERIAL Anilide | Sulfonyl Halide | PRODUCT |
|---|---|---|---|
| 12 | 4-trifluoromethylperfluoromethanesulfonanilide | methanesulfonyl chloride | N-methylsulfonyl-4-trifluoromethylperfluoroethanesulfonanilide |
| 13 | 4-acetyltrifluoromethanesulfonanilide | chloromethanesulfonyl chloride | N-chloromethanesulfonyl-4-acetyltrifluoromethanesulfonanilide |
| 14 | 3-cyanotrifluoromethanesulfonanilide | difluoromethanesulfonyl chloride | N-difluoromethanesulfonyl-3-cyanotrifluoromethanesulfonanilide |
| 15 | 2-methylsulfinyltrifluoromethanesulfonanilide | ethanesulfonyl chloride | N-ethanesulfonyl-2-methylsulfinyltrifluoromethanesulfonanilide |
| 16 | 3-methylsulfonylperfluoroethanesulfonanilide | butanesulfonyl chloride | N-butanesulfonyl-3-methylsulfonylperfluoroethanesulfonanilide |
| 17 | 5-chloro-2,4-dimethoxytrifluoromethanesulfonanilide | methanesulfonyl chloride | N-methylsulfonyl-5-chloro-2,4-dimethoxytrifluoromethanesulfonanilide |
| 18 | 2-(2,2,2-trifluoroethoxy)trifluoromethanesulfonanilide | chloromethanesulfonyl chloride | N-chloromethanesulfonyl-2-(2,2,2-trifluoroethoxy)trifluoro-methanesulfonanilide |
| 19 | 4-(2,2,2-trifluoroethylthio)trifluoromethanesulfonanilide | methanesulfonyl chloride | N-methylsulfonyl-4-(2,2,2-trifluoroethylthio)trifluoromethanesulfonanilide |
| 20 | 4-trifluoromethylthiotrifluoromethanesulfonanilide | perfluoroethanesulfonyl chloride | N-perfluoroethylsulfonyl-4-trifluoromethylthiotrifluoromethanesulfonanilide |
| 21 | 2-(n-butyroyl)trifluoromethanesulfonanilide | trifluoromethanesulfonyl chloride | N-trifluoromethylsulfonyl-2-(n-butyroyl)trifluoromethanesulfonanilide |
| 22 | 4-trifluoromethylsulfonyltrifluoromethanesulfonanilide | methanesulfonyl chloride | N-methylsulfonyl-4-trifluoromethylsulfonyltrifluoromethanesulfonanilide |
| 23 | 3-trifluoromethylsulfonoxytrifluoromethanesulfonanilide | methanesulfonyl chloride | N-methylsulfonyl-3-trifluoromethylsulfonoxytrifluoro |

TABLE II-continued

| Ex. No. | STARTING MATERIAL Anilide | Sulfonyl Halide | PRODUCT |
|---|---|---|---|
| 24 | 2,3,4,5,6-pentafluoro-trifluoromethanesulfonanilide | methanesulfonyl chloride | methanesulfonanilide N-methylsulfonyl-2,3,4,5,6-pentafluoro-trifluoromethanesulfonanilide |
| 25 | 2,4-bis(methylthio)trifluoromethanesulfonanilide | methanesulfonyl chloride | N-methylsulfonyl-2,4-bis(methylthio)trifluoromethanesulfonanilide |

We claim:

1. A compound of the formula

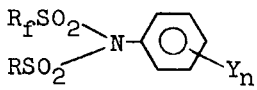

wherein $R_f$ is perfluoroalkyl of 1 to 2 carbon atoms, R is lower alkyl or lower haloalkyl, Y is selected from halogen, nitro, cyano, alkyl, haloalkyl, alkoxy, haloalkoxy, alkylthio, haloalkylthio, alkanoyl, haloalkanoyl, alkanoylamino, haloalkanoylamino, alkylsulfinyl, haloalkylsulfinyl, alkylsulfonyl, haloalkylsulfonyl, alkylsulfonoxy and haloalkylsulfonoxy and $n$ is 0–5, provided that the R and Y moieties contain not more than four carbon atoms each.

2. A compound according to claim 1 wherein $R_f$ is trifluoromethyl.

3. A compound according to claim 1 wherein R contains one carbon atom.

4. A compound according to claim 2 wherein R is methyl.

5. A compound according to claim 3 wherein $R_f$ is trifluoromethyl.

6. A compound according to claim 5 wherein Y is halogen.

7. N-methylsulfonyl-4-fluorotrifluoromethanesulfonanilide according to claim 6.

8. A compound according to claim 5 wherein Y is haloalkyl.

9. A compound according to claim 5 wherein Y is alkylthio.

10. N-methylsulfonyl-4-methylthiotrifluoromethanesulfonanilide according to claim 9.

* * * * *